(12) United States Patent
Ameer et al.

(10) Patent No.: US 11,559,609 B2
(45) Date of Patent: Jan. 24, 2023

(54) BONE-PROMOTING THERMORESPONSIVE MACROMOLECULES

(71) Applicant: Northwestern University, Evanston, IL (US)

(72) Inventors: Guillermo A. Ameer, Chicago, IL (US); Simona Morochnik, Chicago, IL (US)

(73) Assignee: Northwestern Univesity, Evanston, IL (US)

( * ) Notice: Subject to any disclaimer, the term of this patent is extended or adjusted under 35 U.S.C. 154(b) by 288 days.

(21) Appl. No.: 16/468,224

(22) PCT Filed: Dec. 8, 2017

(86) PCT No.: PCT/US2017/065352
§ 371 (c)(1),
(2) Date: Jun. 10, 2019

(87) PCT Pub. No.: WO2018/107049
PCT Pub. Date: Jun. 14, 2018

(65) Prior Publication Data
US 2019/0336648 A1 Nov. 7, 2019

Related U.S. Application Data

(60) Provisional application No. 62/571,495, filed on Oct. 12, 2017, provisional application No. 62/432,266, filed on Dec. 9, 2016.

(51) Int. Cl.
| | | |
|---|---|---|
| A61L 27/52 | (2006.01) | |
| A61K 9/00 | (2006.01) | |
| A61K 9/06 | (2006.01) | |
| A61K 31/661 | (2006.01) | |
| A61K 33/06 | (2006.01) | |
| A61K 38/06 | (2006.01) | |
| A61L 27/54 | (2006.01) | |
| A61K 39/385 | (2006.01) | |
| A61K 39/00 | (2006.01) | |

(52) U.S. Cl.
CPC ............ *A61L 27/52* (2013.01); *A61K 9/0019* (2013.01); *A61K 9/06* (2013.01); *A61K 31/661* (2013.01); *A61K 33/06* (2013.01); *A61K 38/06* (2013.01); *A61K 39/385* (2013.01); *A61L 27/54* (2013.01); *A61K 2039/6093* (2013.01); *A61L 2400/06* (2013.01); *A61L 2430/02* (2013.01)

(58) Field of Classification Search
None
See application file for complete search history.

(56) References Cited

U.S. PATENT DOCUMENTS

2006/0106392 A1    5/2006  Embry
2016/0346382 A1   12/2016  Bryce et al.

FOREIGN PATENT DOCUMENTS

| WO | WO 2000/023123 | 4/2000 | |
|---|---|---|---|
| WO | WO 2008/131154 | 10/2008 | |
| WO | WO 2009/030919 | 3/2009 | |
| WO | WO 2012106317 | 8/2012 | |
| WO | WO 2016100847 | 6/2016 | |
| WO | WO-2016100847 A2 * | 6/2016 | ............. A61L 15/44 |
| WO | WO 2016183277 | 11/2016 | |

OTHER PUBLICATIONS

Langenbach F and Handschel J "Effects of dexamethasone, ascorbic acid and B-glycerophosphate on the osteogenic differentation of stem cells in vitro" Stem Cell Research & Therapy 4:117 (Year: 2013).*
Yang et al. "A Thermoresponsive Biodegradable Polymer with Intrinsic Antioxidant Properties" Blomacromolecules 15:3942-3952. (Year: 2014).*
Wauquier et al. "Oxidative stress in bone remodelling and disease" Trends in Molecular Medicine 15:468-477. (Year: 2009).*
Ye et al., A thermoresponsive polydiolcitrate-gelatin scaffold and delivery system mediates effective bone formation from BMP9-transduced mesenchymal stem cells. Biomed Mater. Apr. 21, 2016;11(2):025021.
Arshady, Preparation of biodegradable microspheres and microcapsules: 2. Polyactides and related polyesters, Controlled Release, 1991. 17:1-22.
Bhatnagar et al., Design of biomimetic habitats for tissue engineering with P-15, a synthetic peptide analogue of collagen, Tissue Eng. Feb. 1999;5(1):53-65.
Holland et al., Polymers for biodegradable medical devices. 1. The potential of polyesters as controlled macromolecular release systems, J. Controlled Release 1986. 4:155-0180.
Illum et al., (eds.) "Polymers in Controlled Drug Delivery" Wright, Bristol, 1987, TOC only.
Morochnik et al., A thermoresponsive, citrate-based macromolecule for bone regenerative engineering. Society for Biomaterials. 2018. 1743-1752.
Pitt, The controlled parenteral delivery of polypeptides and proteins, Int. J. Phar. 1990;59:173-196.
Pountos et al., The role of peptides in bone healing and regeneration: a systematic review, BMC Med. Jul. 11, 2016;14:103.

(Continued)

*Primary Examiner* — Sudhakar Katakam
*Assistant Examiner* — Zachary J Miknis
(74) *Attorney, Agent, or Firm* — Casimir Jones SC; David W. Staple

(57) ABSTRACT

Provided herein are injectable, thermoresponsive hydrogels that are liquid at room temperature, provide a carrier material, and gel at body temperature to allow for controlled release. In particular, PPCN-based hydrogels are provided with therapeutic agents (e.g., drugs, ions, etc.) incorporated within or appended thereto, and methods of preparation and use thereof, for example, for the promotion of bone formation/repair and/or the treatment of bone diseases.

4 Claims, 8 Drawing Sheets
(7 of 8 Drawing Sheet(s) Filed in Color)
Specification includes a Sequence Listing.

(56) References Cited

OTHER PUBLICATIONS

Ruoslahti et al., Arg-Gly-Asp: a versatile cell recognition signal, Cell. Feb. 28, 1986;44(4):517-8.
Zhu et al., Extrahepatic islet transplantation with a citrate-based thermoresponsive hydrogel. New Biotechnol Conference Abstract: 10th World Biomaterials Congress. 2016. 4 pages.
International Search Report and Written Opinion for PCT/US17/65352. dated Feb. 20, 2018. 10 pages.
Extended European Search Report for PCT/US2017/065352. dated Sep. 6, 2020. 10 pages.
Chung et al., Mechanism of action of beta-glycerophosphate on bone cell mineralization. Calcif Tissue Int. Oct. 1992;51(4):305-11.
Wang et al., Thermogelling chitosan and collagen composite hydrogels initiated with beta-glycerophosphate for bone tissue engineering. Biomaterials. May 2010;31(14):3976-85.
Yang et al., A thermoresponsive biodegradable polymer with intrinsic antioxidant properties. Biomacromolecules. Nov. 10, 2014;15(11):3942-52.

\* cited by examiner

BONE-PROMOTING THERMORESPONSIVE MACROMOLECULES

CROSS-REFERENCE TO RELATED APPLICATIONS

The present invention is a § 371 U.S. National Entry application based on PCT/US2017/065352, filed Dec. 8, 2017, which claims priority to U.S. Provisional Patent Application Ser. No. 62/432,266, filed Dec. 9, 2016, and to U.S. Provisional Patent Application Ser. No. 62/571,495, filed Oct. 12, 2017, each of which are incorporated by reference in their entireties.

FIELD

Provided herein are injectable, thermoresponsive hydrogels that are liquid at room temperature, provide a carrier material, and gel at body temperature to allow for controlled release. In particular, PPCN-based hydrogels are provided with therapeutic agents (e.g., drugs, ions, etc.) incorporated within or appended thereto, and methods of preparation and use thereof, for example, for the promotion of bone formation/repair and/or the treatment of bone diseases.

BACKGROUND

Significant focus in the field of bone tissue engineering has been placed on developing materials for repair of bone defects. Much less work has been directed toward bone diseases. As such, material strength has been the main focus rather than the material's ability to induce bone formation. These materials are often hard, filler pastes that are biologically inert (e.g., methyl methacrylate) or brittle (e.g., calcium phosphate). Additionally, the challenges of inflammation and osteoporotic bone have been largely unexplored. An unmet need lies in the development of materials that can be used with a minimally invasive procedure to conform to unique fracture sites, can interact with the complex cellular environment to accelerate healing in all bone types, induce stem cells to become bone cells, and allow for localized drug delivery if necessary.

SUMMARY

Provided herein are injectable, thermoresponsive hydrogels that are liquid at room temperature, provide a carrier material, and gel at body temperature to allow for controlled release. In particular, PPCN-based hydrogels are provided with therapeutic agents (e.g., drugs, ions, etc.) incorporated within or appended thereto, and methods of preparation and use thereof, for example, for the promotion of bone formation/repair and/or the treatment of bone diseases.

In some embodiments, provided herein are compositions comprising a PPCN-based hydrogel comprising citric acid, poly(ethylene glycol), glycerol 1,3-diglycerolate diacrylate, and poly-(N-isopropylacrylamide) monomers and at least one bioactive agent incorporated therein and/or appended thereto. In some embodiments, the bioactive agent is an additional monomer incorporated into the PPCN-based hydrogel backbone. In some embodiments, the bioactive agent is β-glycerophosphate. In some embodiments, the bioactive agent is a pendant group appended to a PPCN hydrogel. In some embodiments, the pendant group is a small molecule. In some embodiments, the pendant group is a peptide. In some embodiments, the bioactive agent is a cyclic Arg-Gly-Asp (cRGD) peptide. In some embodiments, the bioactive agent is an ionic crosslinking agent. In some embodiments, the bioactive agent is $Ca^{2+}$, $Ba^{2+}$, or $Sr^{2+}$.

In some embodiments, provided herein are compositions comprising a PPCN-based phosphate-displaying hydrogel comprising citric acid, poly(ethylene glycol), glycerol 1,3-diglycerolate diacrylate, poly-(N-isopropylacrylamide), and β-glycerophosphate monomers. In some embodiments, the PPCN-based phosphate-displaying hydrogel comprises the structure:

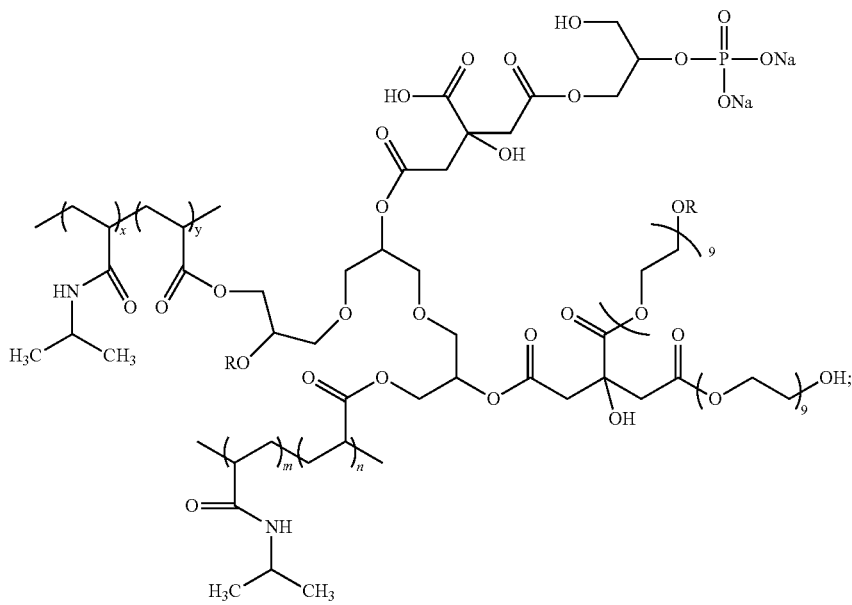

wherein x and y are independently 2-20. In some embodiments, the composition is prepared by (a) polycondensation of citric acid, poly(ethylene glycol), glycerol 1,3-diglycerolate diacrylate, and β-glycerophosphate monomers; followed by (b) free radical polymerization with poly-(N-isopropylacrylamide). In some embodiments, the composition is prepared by the reactions depicted in Scheme 1.

In some embodiments, provided herein are compositions comprising a PPCN-based peptide-displaying hydrogel comprising citric acid, poly(ethylene glycol), glycerol 1,3-diglycerolate diacrylate, and poly-(N-isopropylacrylamide) monomers, and a peptide covalently conjugated to carboxy groups of the citric acid monomers. In some embodiments, the peptide is covalently conjugated via carbodiimide chemistry to carboxy groups of the citric acid monomers. In some embodiments, the peptide is cyclic Arg-Gly-Asp (cRGD). In some embodiments, the cRGD is covalently conjugated to carboxy groups of PPCN. In some embodiments, the composition is prepared by reactions depicted in Scheme 2.

In some embodiments, provided herein are compositions comprising a PPCN-based hydrogel comprising citric acid, poly(ethylene glycol), glycerol 1,3-diglycerolate diacrylate, and poly-(N-isopropylacrylamide) monomers, and metal ion crosslinks. In some embodiments, compositions comprise metal-ion-crosslinked PPCN. In some embodiments, compositions are prepared by incubating the PPCN in the presence of a salt of the metal ion. In some embodiments, the metal ion is $Ca^{2+}$, $Ba^{2+}$, or $Sr^{2+}$.

In some embodiments, provided herein are methods of facilitating bone repair comprising administering a composition described herein (e.g., a PPCN-based hydrogel) to fractured or diseased bone site, and allowing the composition to gel.

In some embodiments, provided herein is the use of a composition described herein (e.g., a PPCN-based hydrogel) to facilitate bone repair.

BRIEF DESCRIPTION OF THE DRAWINGS

The patent or application file contains at least one drawing executed in color. Copies of this patent or patent application publication with color drawings will be provided by the Office upon request and payment of the necessary fee.

DEFINITIONS

Figure 1:
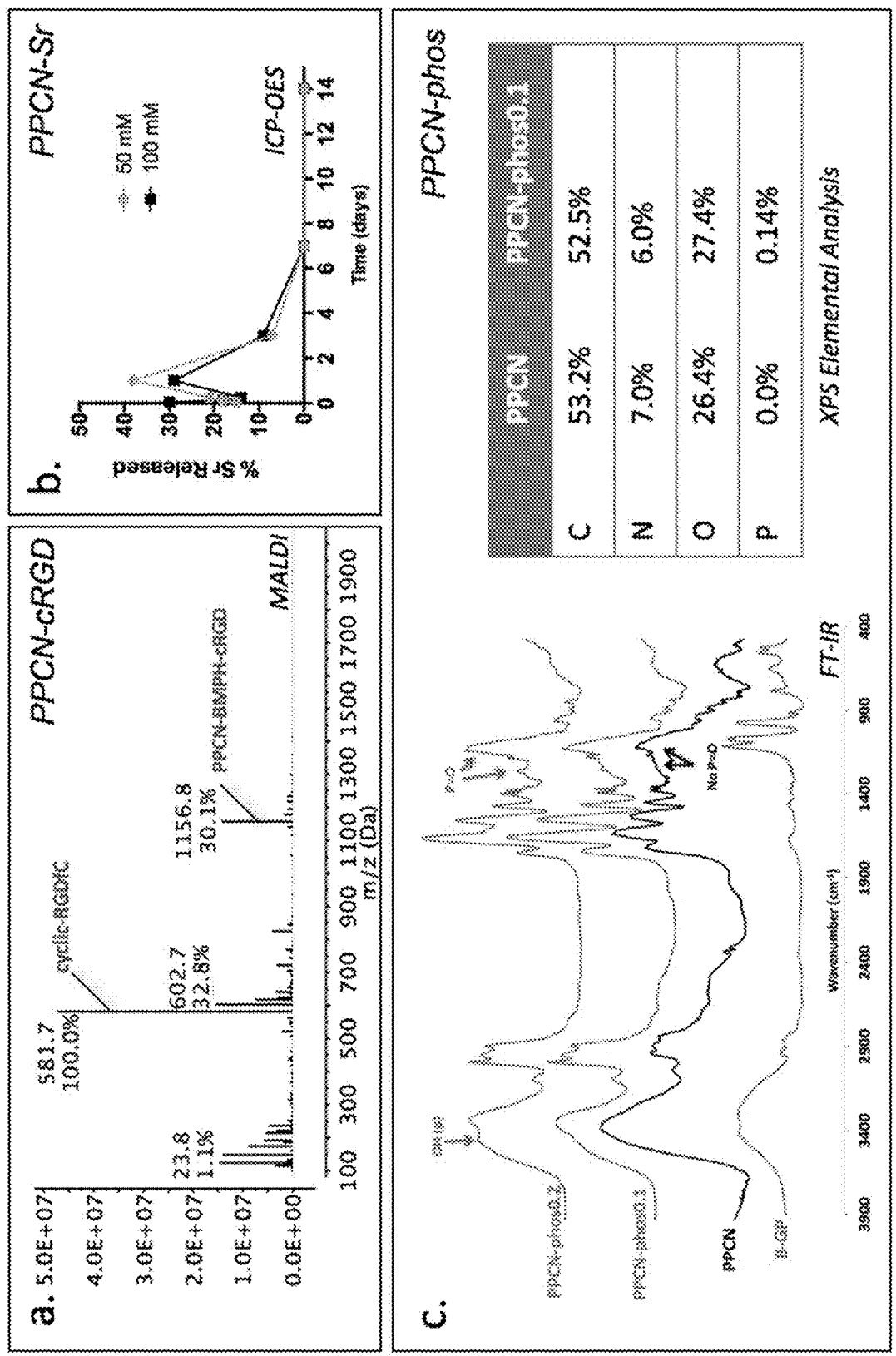
FIG. 1. (a) MALDI spectrum of PPCN-cRGD major peaks include expected ionized cyclic-RGDfC at 581.7 m/z and full monomer at 1156 m/z. (b) ICP-OES of 50 mM and 100 mM $Sr^{2+}$ release from PPCN-Sr gels reveals majority of strontium is released in 1 week. FT-IR of PPCN-phos shows growth of peaks associated with reagent β-glycerophosphate, namely the broadening of the OH stretch at 3400 $nm^{-1}$ and growth of a new peak around 1238 $nm^{-1}$ attributed to phosphonate. Elemental analysis corroborates this data with a small reduction in carbon due to the displacement of carbon-rich PEG chains by β-glycerophosphate.
Figure 2:
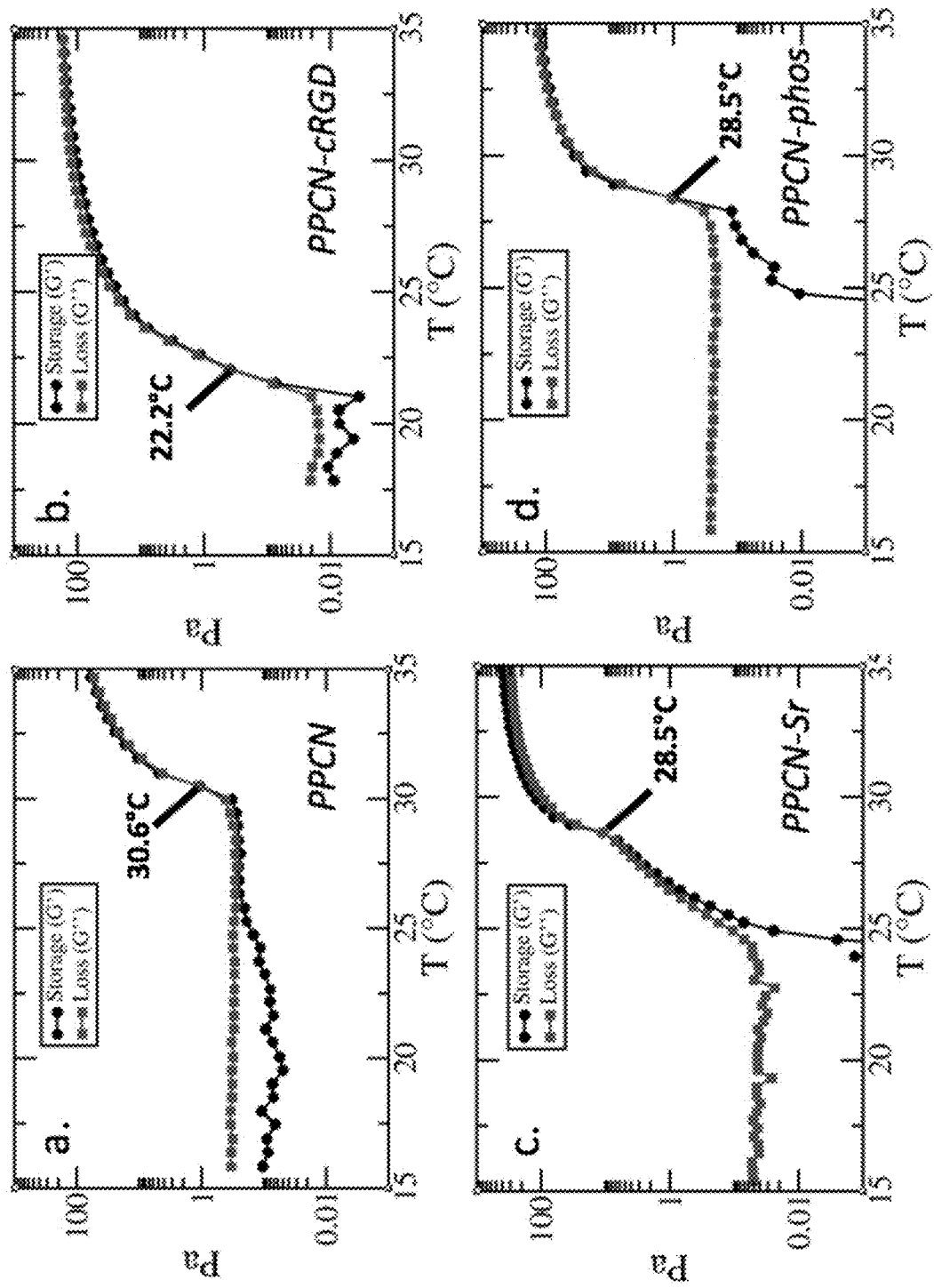
FIG. 2. Rheological characterization of PPCN (a) as compared to PPCN-cRGD (b), PPCN-Sr (c) and PPCN-phos (d) confirms that all three osteoinductive variants maintain thermoresponsive behavior and exhibit a lower LCST transition than PPCN.
Figure 3:
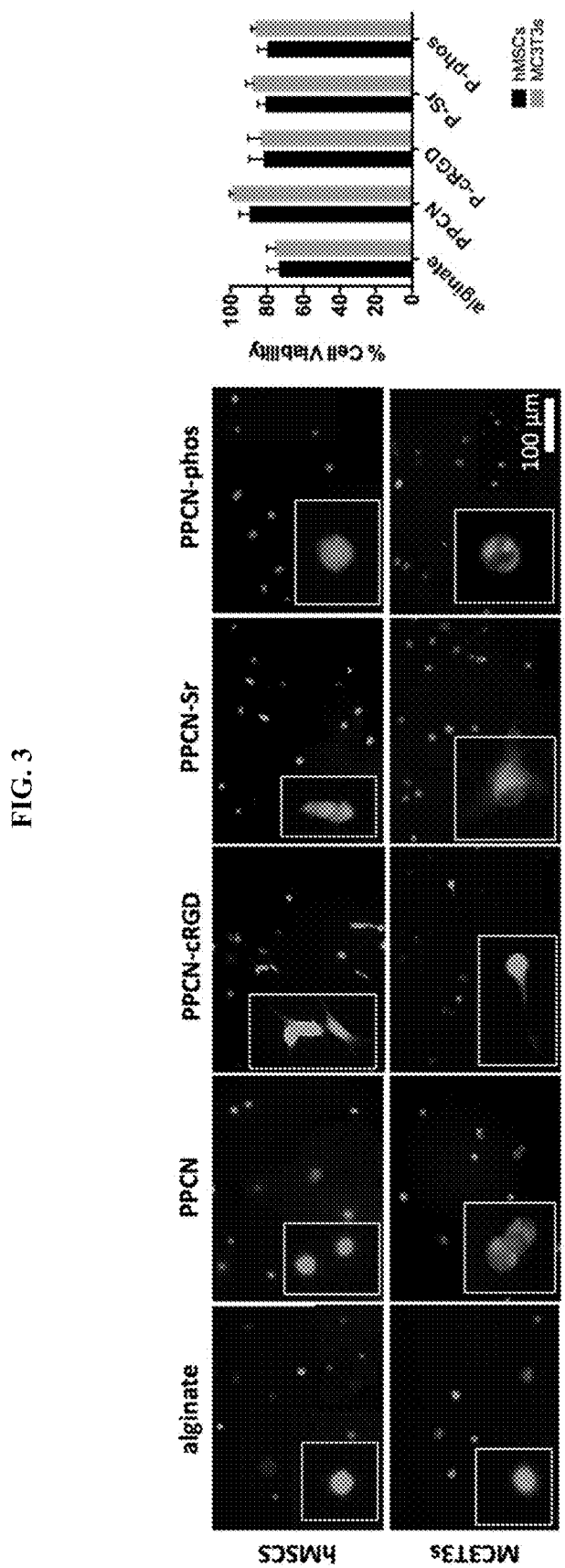
FIG. 3. LIVE/DEAD imaging of hMSCs and MC3T3s seeded in 3D gels and cultured in regular DMEM. Cells were seeded in either alginate, PPCN, PPCN-cRGD, PPCN-Sr, or PPCN-phos gels. Cells grown in PPCN-cRGD gels show spreading morphology confirming the functionality of RGD is preserved post-conjugation. Viability in all gels is above 75%. Images were taken at day 10 and representative images shown from n=3 wells.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a polymer" is a reference to one or more polymers and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C." As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially all," "substantially complete" and similar terms refer to greater than 99%; and the terms "substantially none," "substantially free of," and similar terms refer to less than 1%.

The term "about" allows for a degree of variability in a value or range. As used herein, the term "about: refers to values within 10% of the recited value or range (e.g., about 50 is the equivalent of 45-55).

As used herein, the term "polymer" refers to a chain of repeating structural units or "monomers", typically of large molecular mass. Examples of polymers include homopolymers (single type of monomer subunits), copolymers (two types of monomer subunits), and heteropolymers (e.g., three or more types of monomer subunits). As used herein, the term "oligomer" refers to a polymer of only a few monomer units (e.g., 2, 3, 4, 5, or more) up to about 50 monomer units, for example a dimer, trimer, tetramer, pentamer, hexamer . . . decamer, etc.

As used herein, the term "linear polymer" refers to a polymer in which the molecules form long chains without branches or crosslinked structures.

As used herein, the term "branched polymer" refers to a polymer comprising a polymer backbone with one or more additional monomers, or chains or monomers, extending from polymer backbone. The degree of interconnectedness of the "branches" is insufficient to render the polymer insoluble.

As used herein, the term "pre-polymer" refers to linear or branched polymers (e.g., not significantly crosslinked) that have the capacity to be crosslinked under appropriate conditions (e.g., to "cure" and/or form a thermoset or hydrogel), but have not been subjected to the appropriate conditions.

As used herein, the term "crosslinked polymer" refers to a polymer with a significant degree of interconnectedness between multiple polymer strands, the result of which is an insoluble polymer network. For example, multiple polymer stands may be crosslinked to each other at points within their structures, not limited to the ends of the polymer chains.

As used herein, the term "biocompatible" refers to materials, compounds, or compositions means that do not cause or elicit significant adverse effects when administered to a subject. Examples of possible adverse effects that limit biocompatibility include, but are not limited to, excessive inflammation, excessive or adverse immune response, and toxicity.

As used herein, the term "hydrogel" refers to a three-dimensional (3D) crosslinked network of hydrophilic polymers that swells, rather than being dissolved, in water.

As used herein, the term "thermoresponsive" refers to material that exhibit altered physical characteristics at different temperature ranges. Particularly relevant herein are "phase-transitioning thermoresponsive" materials. Phase-transitioning thermoresponsive" materials are soluble or in a liquid state at a first temperature range (e.g., below 26° C.) and insoluble or in a solid state at a second temperature range (e.g., 30-45° C.).

DETAILED DESCRIPTION

Provided herein are injectable, thermoresponsive hydrogels that are liquid at room temperature, provide a carrier material for ions or therapeutics, and gel at body temperature to allow for controlled release. In some embodiments, materials are antioxidant and can promote bone formation based on material properties, without osteogenic supplementation. In some embodiments, materials comprise, for example, bone-promoting agents, such as phosphate, cRGD, and/or strontium.

In some embodiments, provided herein are thermoresponsive hydrogels comprising citric acid, poly(ethylene glycol), glycerol 1,3-diglycerolate diacrylate, and poly-(N-isopropylacrylamide) monomers. In some embodiments, thermoresponsive hydrogels are PPCN-based hydrogels. In some embodiments, a PPCN-based hydrogel comprises citric acid, poly(ethylene glycol), glycerol 1,3-diglycerolate diacrylate, and poly-(N-isopropylacrylamide) monomers and one or more additional monomer groups (e.g., (3-glycerophosphate). In some embodiments, a PPCN-based hydrogel comprises citric acid, poly(ethylene glycol), glycerol 1,3-diglycerolate diacrylate, and poly-(N-isopropylacrylamide) monomers and is conjugated to one or more bioactive agents (e.g., metal ions (e.g., $Sr^{2+}$), peptides (e.g., cRGD), etc.).

In some embodiments, negatively-charged carboxyl groups on the PPCN-based hydrogels (e.g., displayed on the citric acid monomers) conjugate positively charged metal ions (e.g., $Sr^{2+}$, $Ca^{2+}$, $Ba^{2+}$, etc.). In some embodiments, coordination of metal ions by separate carboxyl groups results in crosslinks in the PPCN-based polymer. In some embodiments, materials herein are not limited by the identity of the metal ion. In some embodiments, metal ions are introduced as salts to the PPCN-based materials.

In some embodiments, carboxyl groups on the PPCN-based hydrogels (e.g., displayed on the citric acid monomers) are conjugated via appropriate linker chemistry to peptides or bioactive small molecules. In some embodiments, suitable chemistries for linking bioactive peptides and/or small molecules to the PPCN-based hydrogels include alkyne/azide, thiol/maleimide, thiol/haloacetyl (e.g., iodoacetyl, etc.), thiol/pyridyl disulfide (e.g. pyridyldithiol, etc.), sulphonyl azides/thio acids, etc.

In some embodiments, a bioactive peptide that facilitate bone healing and/or repair is conjugated to a PPCN-based hydrogel. Suitable peptides include the P-15 peptide (Bhatnagar et al. Tissue Eng. 1999; 5(1):53-65; incorporated by reference in its entirety), an RGD containing peptide (Ruoslahti & Pierschbacher. Cell. 1986; 44(4):517-8; incorporated by reference in its entirety), GFOGER (glycine-phenylalanine-hydroxyproline-glycine-glutamate-arginine)

(SEQ ID NO: 1), collagen-binding motif (CBM), DGEA (Asp-Gly-Glu-Ala) (SEQ ID NO: 2), SVVYGLR (Ser-Val-Val-Tyr-Gly-Leu-Arg) (SEQ ID NO: 3), KRSR (lysine-arginine-serine-arginine) (SEQ ID NO: 4), FHRRIKA (Phe-His-Arg-Arg-Ile-Lys-Ala) (SEQ ID NO: 5), Fibronectin (FN)-derived peptides, and other ECM-derived peptides (Pountos et al. BMC Med. 2016; 14: 103; incorporated by reference in its entirety).

In some embodiments, PPCN or a PPCN-based polymer or hydrogel comprises comprise at least 0.1% citric acid monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% citric acid monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% citric acid monomers.

In some embodiments, PPCN or a PPCN-based polymer or hydrogel comprises comprise at least 0.1% polyethylene glycol monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% polyethylene glycol monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% polyethylene glycol monomers.

In some embodiments, PPCN or a PPCN-based polymer or hydrogel comprises at least 0.1% glycerol 1,3-diglycerolate diacrylate monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% glycerol 1,3-diglycerolate diacrylate monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% glycerol 1,3-diglycerolate diacrylate monomers.

In some embodiments, PPCN or a PPCN-based polymer or hydrogel comprises at least 0.1% N-isopropylacrylamide monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% N-isopropylacrylamide monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% N-isopropylacrylamide monomers.

In some embodiments, materials described herein comprise composites of the PPCN-based thermoresponsive hydrogel materials described herein and one or more additional components. In some embodiments, additional components comprise 1-99 wt % of the composite material (e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or ranges therebetween). In some embodiments, a composite material comprises at least 1% (e.g., >>1%, >2%, >3%, >4%, >5%, >10%, >20%, >30%, >40%, >50%, >60%, >70%, >80%, >90%, >95%, >98%, >99%) PPCN-based hydrogel. In some embodiments, a thermoresponsive composite material comprises less than 99% (e.g., <99%, <98%, <95%, <90%, <80%, <70%, <60%, <50%, <40%, <30%, <20%, <10%, <5%, <4%, <3%, <2%, <1%) PPCN-based hydrogel. In some embodiments, a composite material comprises a PPCN-based hydrogel in an amount of about 99%, about 98%, about 95%, about 90%, about 80%, about 70%, about 60%, about 50%, about 40%, about 30%, about 20%, about 10%, about 5%, about 4%, about 3%, about 2%, about 1%, or ranges therebetween. The aforementioned percentages may be wt % or molar %.

In some embodiments, composites of thermoresponsive PPCN-based hydrogel materials and a bioceramic component are provided. Suitable bioceramics include hydroxyapatite (HA; $Ca_{10}(PO_4)_6(OH)_2$), tricalcium phosphate beta (β TCP; $Ca_3(PO_4)_2$), and mixtures of HAP and β TCP.

In some embodiments, composite materials comprise a PPCN-based hydrogel and one or more additional polymeric components. Suitable biodegradeable polymers include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties). Suitable non-biogregradable polymers include silicone rubber, polyethylene, acrylic resins, polyurethane, polypropylene, and polymethylmethacrylate.

As described throughout, provided herein are PPCN-based materials comprising curable (e.g., thermoresponsive) hydrogels and/or and composites thereof. These materials find use in a variety of applications. For example, any application in which it is desired that a material be applied in a liquid and/or soluble form, and then is (rapidly) rendered solid and/or insoluble when exposed to desired conditions (e.g., physiological temperature). Materials described herein find use, for example, in medical and dental bone repair applications, such as, repair of craniofacial injuries, stabilizing complex fractures, promoting bone growth, bone regeneration, as a bone-void filler, adhering implants, etc. In some embodiments, materials find use in non-medical/dental applications. In some embodiments, the PPCN-based materials described herein are liquid at subphysiologic temperatures (e.g., 36° C., 35° C., 34° C., 33° C., 32° C., 31° C., 30° C., 29° C., 28° C., 27° C., 26° C., 25° C., 24° C., 23° C., 22° C., 21° C., 20° C., or lower or ranges therebetween). In some embodiments, the PPCN-based materials described herein gel at or near physiologic temperatures (e.g., 30° C., 31° C., 32° C., 33° C., 34° C., 35° C., 36° C., 37° C., 38° C., 39° C., 40° C., or ranges therebetween).

In some embodiments in which the materials herein are used for the repair, stabilization, regeneration, growth, etc. of bone or bone fractures/injuries, the materials further comprise additional components/agents to facilitate incorporation into bone, bone growth, bone regeneration, etc. In some embodiments, additional components/agents are incorporated into the materials and are subsequently encapsulated within the material upon curing. In such embodiments, additional components/agents are non-covalently associated with the PPCN-based hydrogels and other components of the materials. In other embodiments, additional components/agents are covalently-linked PPCN-based hydrogel.

In some embodiments, the materials described herein find use in the delivery of growth factors or other bioactive agents for the repair of bone defects and/or regeneration of bone. Suitable agents for use in embodiments herein include bone morphogenic proteins (e.g., BMP-1, BMP-2, BMP-4, BMP-6, and BMP-7); members of the transforming growth factor beta (TGF-β) superfamily including, but not limited to, TGF-β1, TGF-β2, and TGF-β3; growth differentiation factors (GDF1, GDF2, GDF3, GDF5, GDF6, GDF7, myostatin/GDF8, GDF9, GDF10, GDF11, and GDF15); vascular endothelial growth factor (VEGF); fibroblast growth factor (FGF); etc. These agent, or others, may be covalently linked to materials described herein or components thereof, non-covalently associated with moieties displayed on materials described herein or components thereof, embedded within materials described herein, etc.

In some embodiments, the PPCN-based hydrogels herein find use as a carrier for therapeutics (e.g., osteoporotic drugs), cells (e.g., stem cells), growth factors, etc. In some embodiments, the PPCN-based hydrogels herein provide controlled, localized delivery of bioactive agents encapsulated therein.

In some embodiments, provided herein are methods comprising administering a composition comprising a PPCN-based hydrogel described herein to a bone defect or fracture. In some embodiments, provided herein is the use of a PPCN-based hydrogel described herein to repair a bone defect or fracture.

In some embodiments, the PPCN-based hydrogels described herein are injected into a fracture site (e.g., during orthopedic surgery) to facilitate and/or accelerate healing.

EXPERIMENTAL

Cell Culture

For gel studies, human mesenchymal stem cells (hMSCs, ATCC) were cultured in Dulbecco's Modified Eagle medium (DMEM) and supplemented with 10% FBS and 5 ml 10× penicillin-streptomycin with no further osteogenic supplementation. hMSCs used in these studies were at passage 6 or below. Murine pre-osteoblast MC3T3-E1 cells (ATCC) were cultured in DMEM:F12. Both cell lines were cultured at 37° C. and 5% carbon dioxide ($CO_2$).

Materials Preparation & Characterization

PPCN (poly (polyethylene glycol citrate-co-N-isopropylacrylamide) was prepared by polycondensation and subsequent radical polymerization.

To prepare PPCN-phos, the original PPCN synthesis was adjusted to add 0.1 molar ratio of β-glycerophosphate in the first polycondensation step (Scheme 1). The subsequent reaction steps were unchanged.

Scheme 1. Synthetic scheme of PPCN-phos synthesis. β-glycerophosphate was added during step 1 (polycondensation) of PPCN synthesis in 0.1 or 0.2 molar ratios. The proposed locations of phosphate attachment are shown - specifically via reaction between the reactive hydroxyls of β-glycerophosphate and the available carboxyl groups of citric acid. PPCN-phos of 0.1 molar ratio was used in subsequent cell studies because higher molar ratios exhibited overcrosslinking.

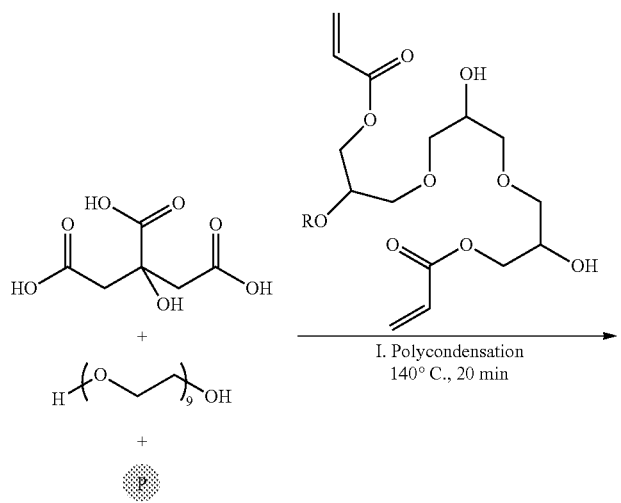

-continued
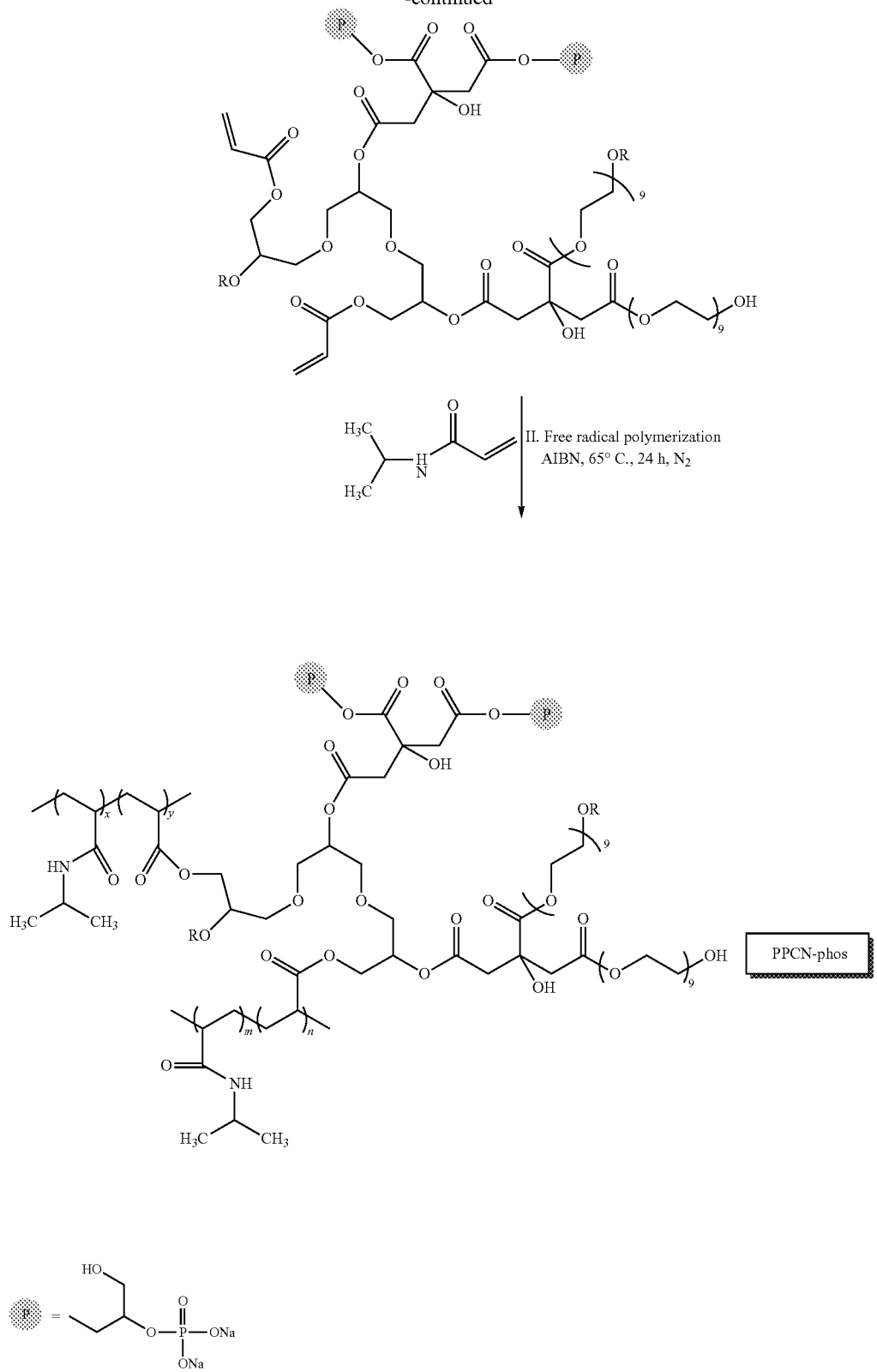
To prepare PPCN-cRGD gels, PPCN was formed as reported. Then, cyclic RGDfC peptide (ABI Scientific) was covalently conjugated via maleimide chemistry to the available carboxy groups of citric acid within the PPCN polymer chain (Scheme 2). The intended density of cyclic RGD peptide was 10%.

Scheme 2. Synthetic scheme of PPCN-Sr and PPCN-cRGD syntheses. PPCN was prepared by polycondensation and subsequent free radical polymerization as previously reported. Then, PPCN-cRGD gels were prepared by covalently conjugating cyclic RGDfC peptide via maleimide chemistry to the available carboxylic acid groups of citric acid within the PPCN polymer chain. To prepare PPCN-Sr gels, PPCN was dissolved in PBS (1x) at 100 mg/ml. 100 mM of SrCl$_2$ 6H$_2$O (Sigma) was mixed into PPCN/PBS solutions and left to crosslink overnight at 4° C. prior to use.

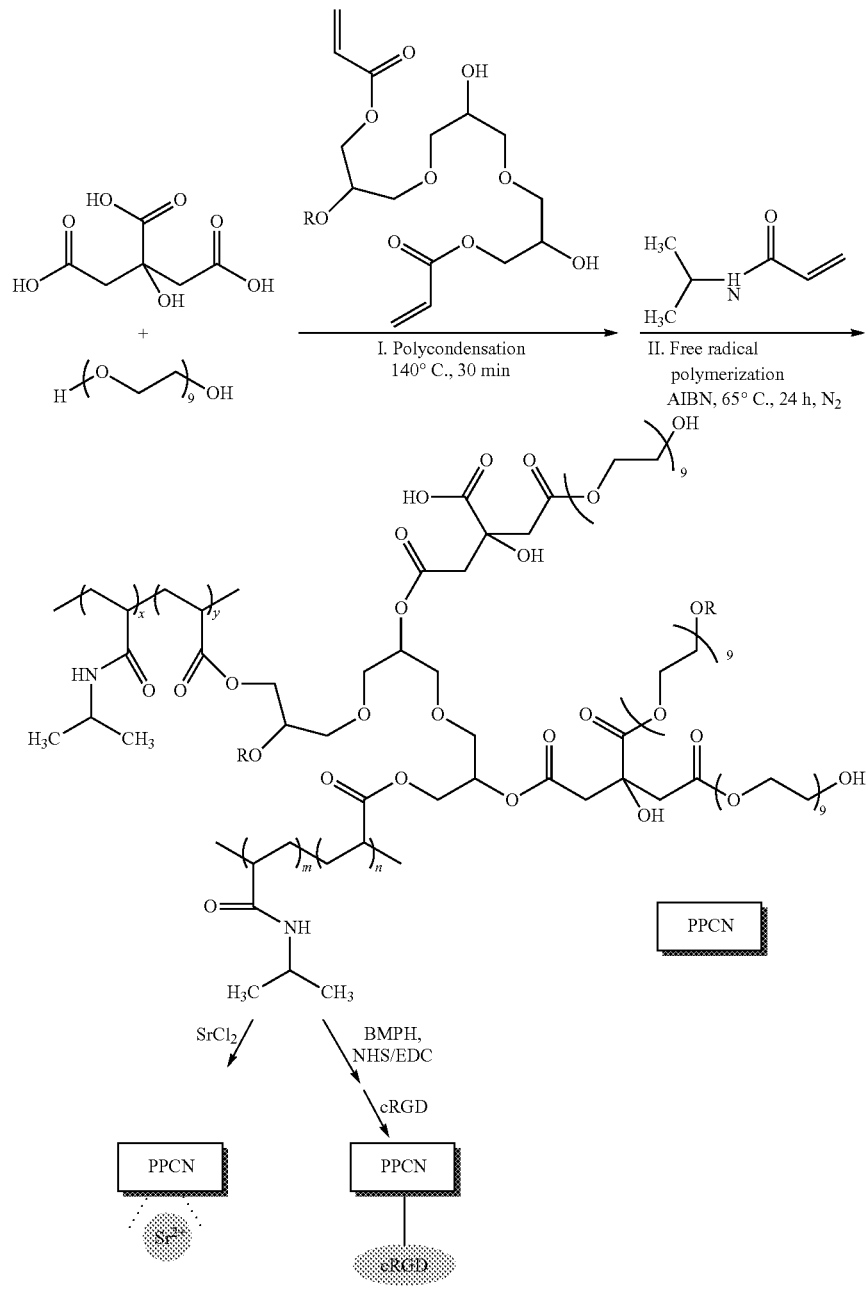

To prepare PPCN-Sr gels, PPCN was dissolved in PBS (1x) at 100 mg/ml. 100 mM of SrCl$_2$ 6H$_2$O (Sigma) was mixed into PPCN/PBS solutions and left to crosslink overnight at 4° C. (Scheme 2).

Characterization for gels is shown in FIG. 1. PPCN-cRGD conjugation was confirmed by matrix assisted laser desorption ionization (MALDI) (FIG. 1a). The samples were prepared with an alpha-cyano-4-hydroxycinnamic acid matrix. PPCN-Sr was characterized by a strontium release study via inductively coupled plasma optical emission spectroscopy (Thermo iCAP 7600 ICP-OES). Gels were immersed in simulated body fluid and solution was removed over a 14 day time course and assayed for Sr$^{2+}$ concentration (FIG. 1b). PPCN-phos was characterized by FT-IR (Bruker Tensor 37) and XPS (FIG. 1c). Further rheological characterization was carried out on a TA instruments DHR rheometer with a 20 mm 2° cone peltier plate geometry and solvent trap cover to minimize sample evaporation. Gels were studied in a temperature ramp experiment from 15° C. to 45° C. with a heating rate of 5° C./min. The viscoelastic moduli were monitored at an applied angular frequency of 10 rad/s and strain amplitude of 5%. A gap height of 52 µm was used for all samples. The initial change in viscoelastic properties was characterized by an increase of storage modulus (G') over loss modulus (G").

3D Differentiation Studies

Cells were encapsulated in various thermoresponsive PPCN solutions of 100 mg/mL PPCN in PBS (lx). Cells were added to solution via uniform mixing at a concentration of $1\times10^5$ cells/mL liquid PPCN. The cell-PPCN mixture was incubated at 37° C. for 5 min to allow gels to form. Once the gel was formed, warm media was added on top and changed every 2 days. Prior to seeding, the plate was coated with Sigma-cote to prevent cell attachment to the plate, ensuring that all cells that persist through media changes persist within the 3D gel environment. During handling, the plates were kept on a plate-warmer to ensure the gel would not be dissolved or diluted as a result of temperature fluctuations. At each time-point, the media was removed and the gel was collected and frozen in the case of ALP and DNA analysis or assayed directly in the case of LIVE/DEAD, alizarin red staining, and immunohistochemistry.

Osteodifferentiation Assays

Figure 4:
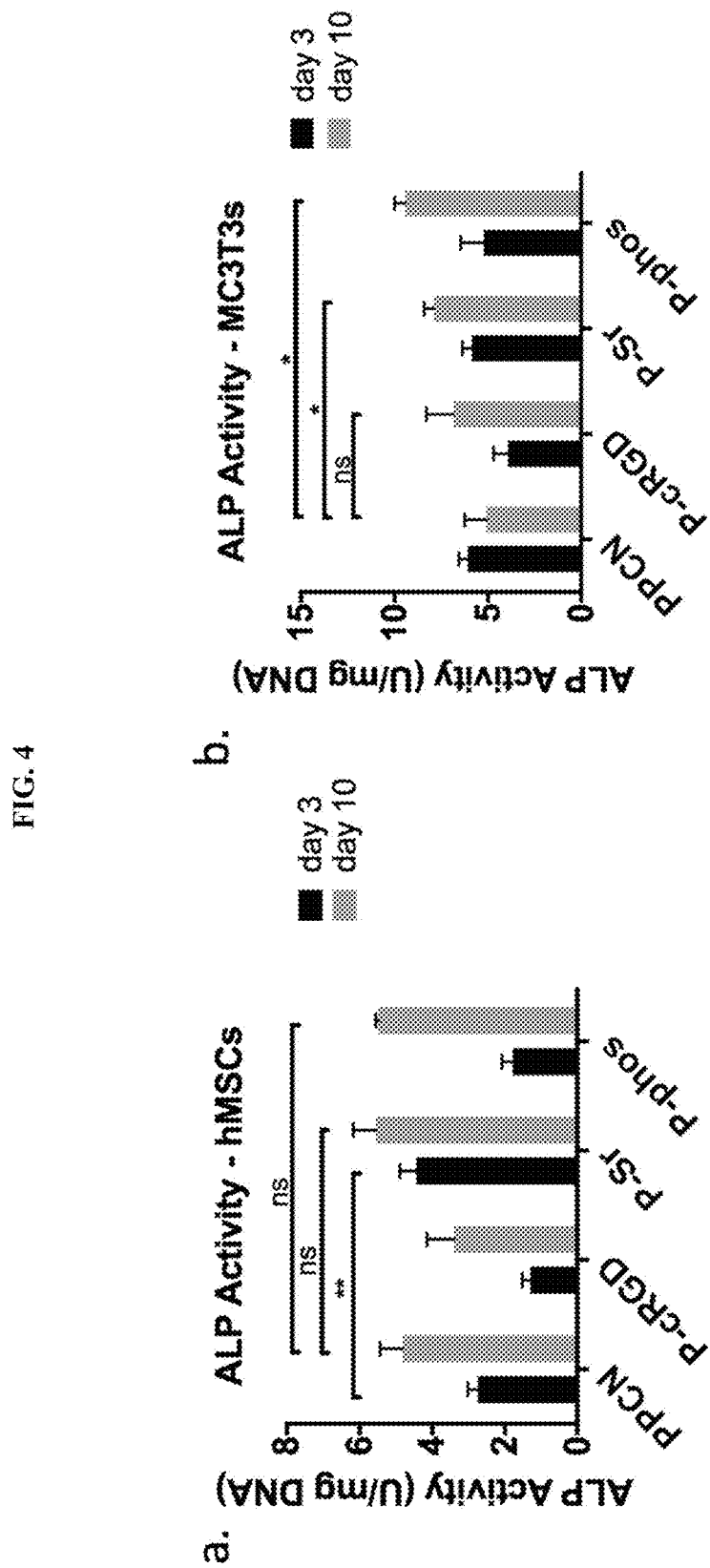
FIG. 4. Day 3 and 10 alkaline phosphatase (ALP) activity shown for (a) hMSCs and (b) MC3T3s. No significant increase in ALP is detected for hMSCs at day 10. However, significant increase in ALP is detected for MC3T3s grown in PPCN-Sr and PPCN-phos gels. *P-value<0.05 and **P-value<0.01.

For early detection of osteodifferentiation (FIG. 4), alkaline phosphatase (ALP) was measured. The gels were collected at day 3 and day 10 and extracellular alkaline phosphatase (ALP) activity was detected by a fluorometric kit (Biovision). A non-fluorescent substrate, 4-Methylumelliferyl phosphate disodium salt (MUP), was added and cleaved by ALP, which results in a fluorescent signal (Ex/Em=360/440 nm). The fluorescence was read on a micro-plate reader. The enzymatic activity was calculated based on serially diluted gel standards and normalized to total DNA content with a concurrent Quant-iT PicoGreen assay (Thermo Fisher).

Figure 5:
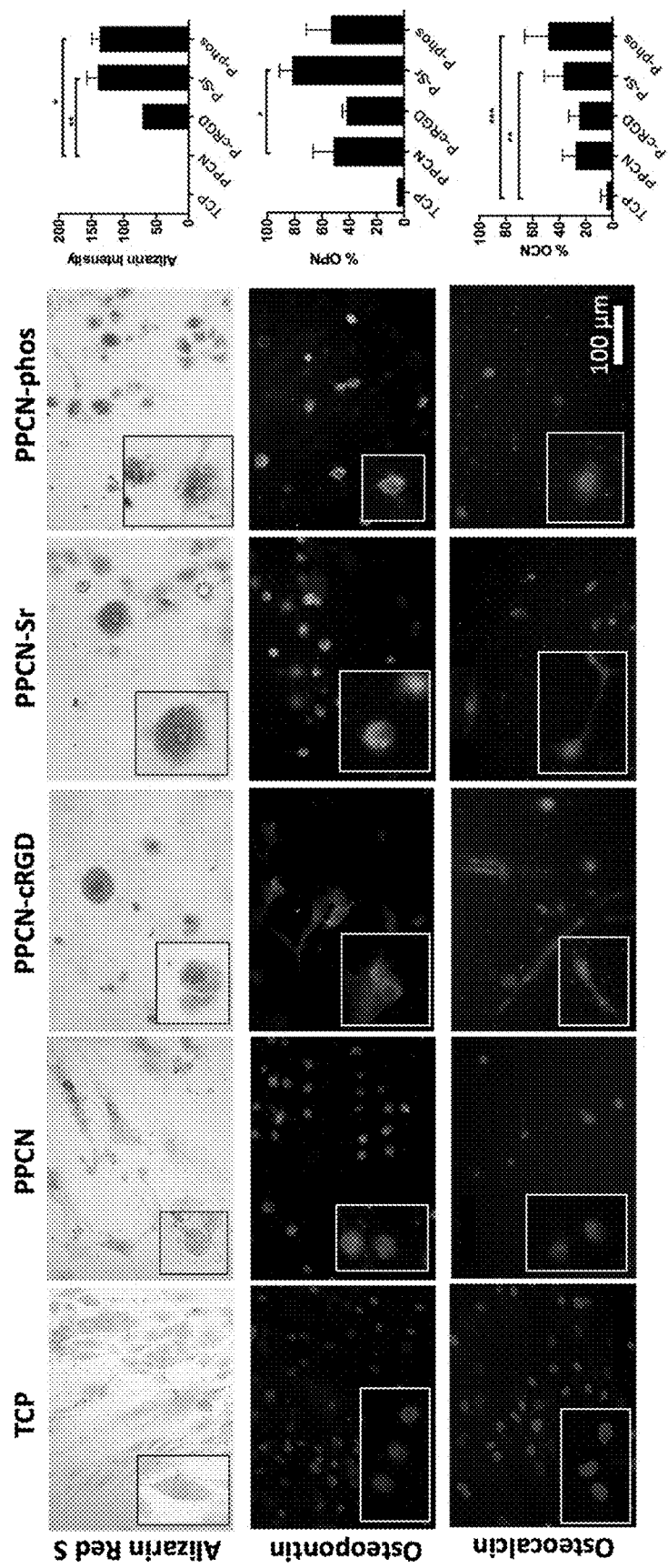
FIG. 5. Day 21 characterization of hMSCs via staining for calcium deposition by Alizarin Red S, immunohistochemistry for osteopontin (OPN), and osteocalcin (OCN). Corresponding quantification is shown on the right. Mineralization is seen in all three functionalizations. From the data, osteopontin expression is highest in PPCN-Sr and osteocalcin expression is highest in PPCN-phos.
Figure 6:
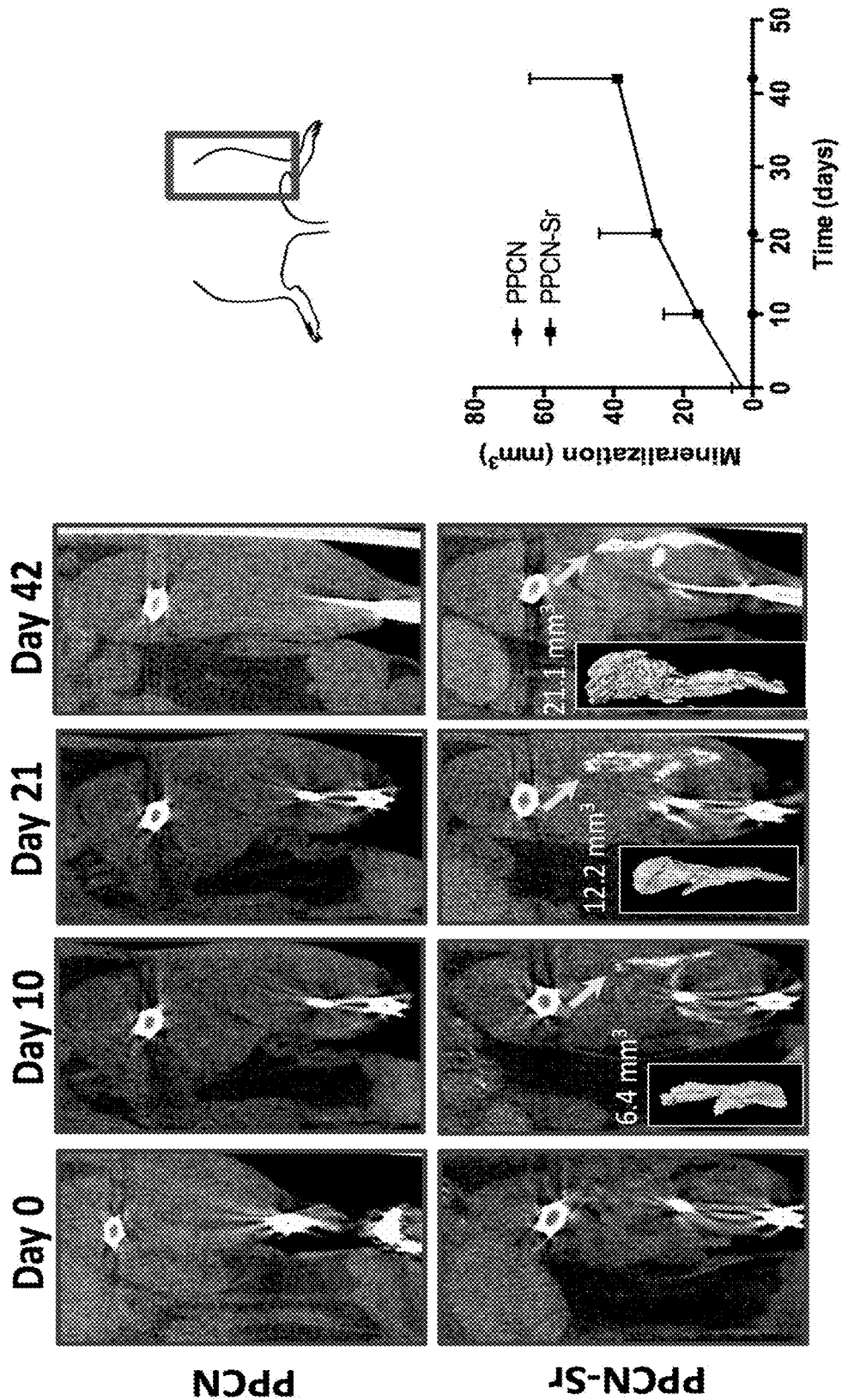
FIG. 6. MicroCT analysis of intramuscular femoral injection of PPCN and PPCN-Sr is shown from day 0 to day 42. The top right panel orients the microCT images onto the mouse femur. The bottom right panel shows the quantification of the microCT images, n=3. Mineralization is observed in the PPCN-Sr group beginning at day 10 and increasing consistently through the 6 week period. No mineralization is observed in the non-functionalized PPCN control. Mineralized regions were quantified with Osirix by threshold intensity and reconstructed to show the 3D inlay.
Figure 7:
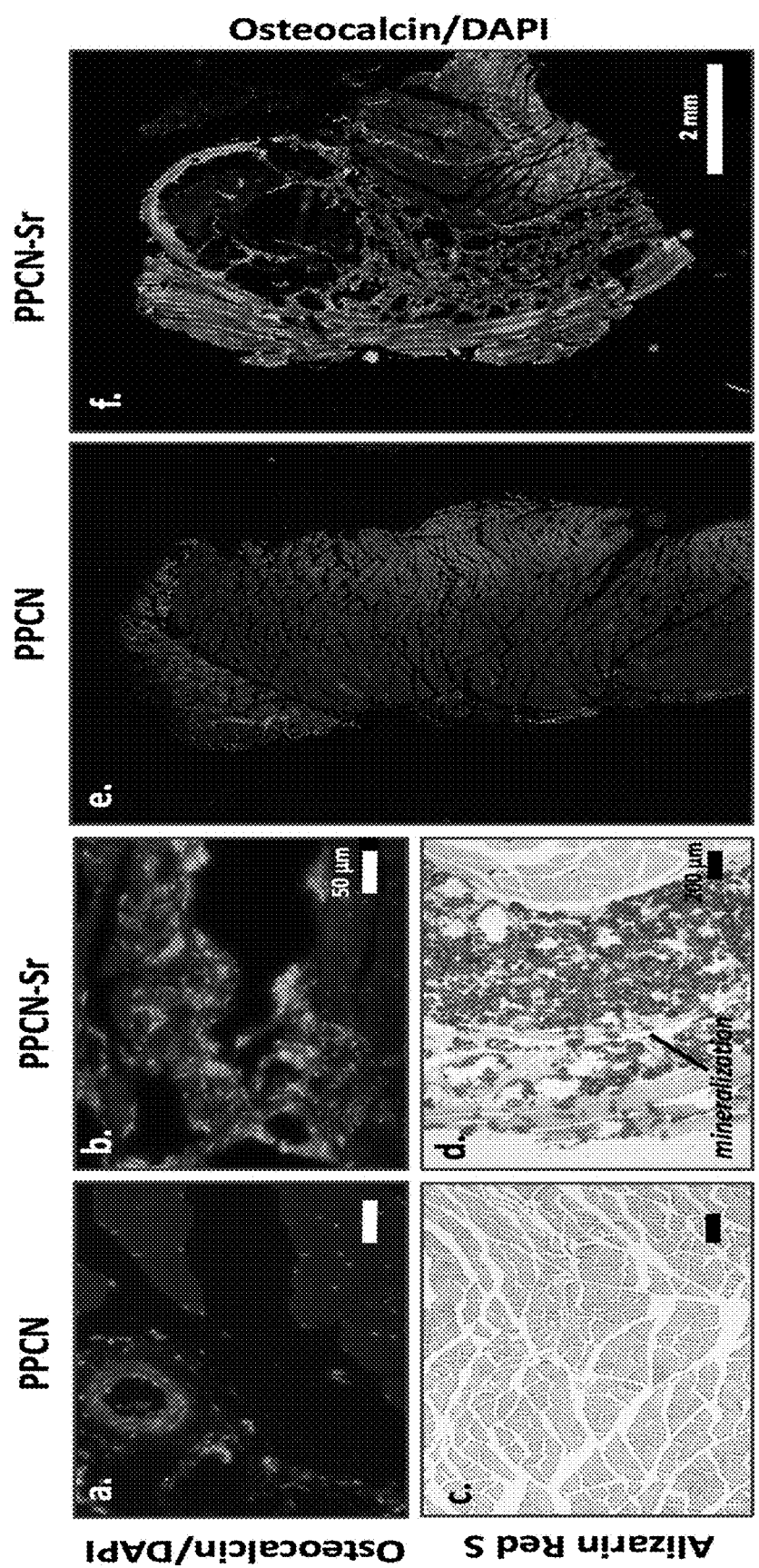
FIG. 7. PPCN-Sr demonstrates significant osteocalcin expression and cell infiltration (b) as compared to PPCN control (a). Alizarin Red S staining for mineralization also demonstrates robust mineralization in PPCN-Sr (d) as detected by red calcium deposits and compared to non-functionalized PPCN (c). Full tissue section is shown for PPCN and PPCN-Sr in (e) and (0, respectively.
Figure 8:
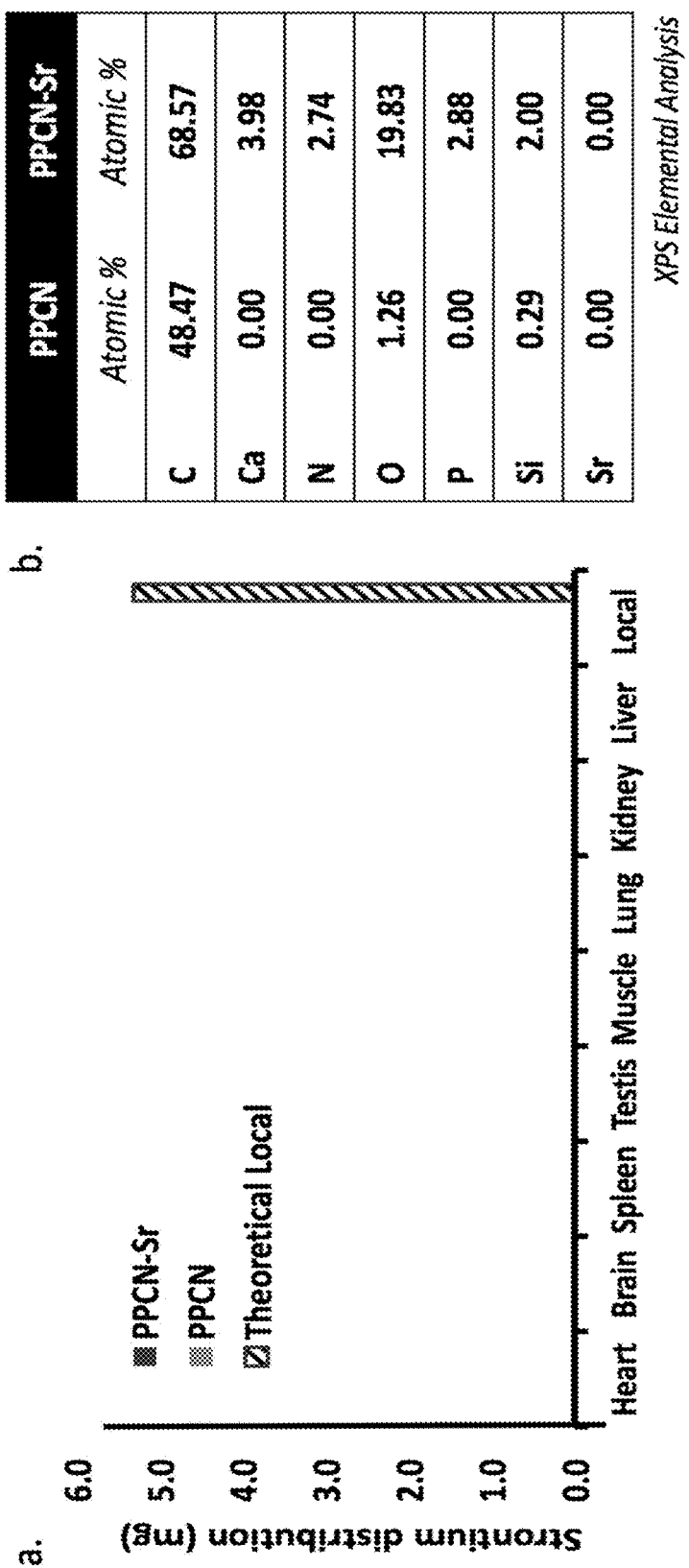
FIG. 8. Day 42 ICP analysis of 8 mouse organs shows that strontium is not present in any of the main organs upon digestion (a). Additionally, XPS analysis of sectioned muscle tissue show that strontium is cleared and no longer present at the site of injection (b). XPS analysis shows calcium, phosphate and oxygen content consistent with mineralization in the PPCN-Sr group, but no local strontium remaining at week 6.

For late detection of osteodifferentiation (FIG. 5), Alizarin Red S staining and immunohistochemistry for osteocalcin (OCN) and osteopontin (OPN) was performed. For Alizarin Red S, the cells were fixed inside the warmed gels and stain was allowed to permeate gels while excess stain was subsequently rinsed out with several washes of DI water. Mineralization was visualized with light microscopy. For immunohistochemistry, the cells were fixed inside the warmed gels and primary antibodies for OPN or OCN were added and counterstained with DAPI.

Mineralization

To assess mineralization, mice were anesthetized with isoflurane and placed on the heated microCT bed. Images were acquired with a preclinical microPET/CT imaging system, nanoScan scanner (Mediso-USA, Boston, Mass.). Data were acquired with "medium" magnification, 33 µm focal spot, 1×1 binning, with 720 projection views over a full circle, with a 300 ms exposure time. Images were acquired using 35 kVp. The projection data was reconstructed with a voxel size of 68 µm using filtered back-projection software from Mediso. The reconstructed data were visualized and segmented in Osirix Lite for Mac. Using the coronal plane, images were quantified by creating regions of interest (ROI) with 2D region-growing using a lower threshold of 600 and an upper threshold of 10,000 Hounsfield units (HU). The regions of interests (ROIs) were used for quantification of mineralization by calculating the mean HU for each ROI (bone is 700 to 3,000 HU).

Immunofluorescence

Animals were euthanized by carbon dioxide inhalation. Tissues were collected and fixed by 4% paraformaldehyde in PBS overnight at 4° C. Samples were washed by PBS with several changes to remove paraformaldehyde residue. The samples were dehydrated by series ethanol, cleared by xylene, and embedded in paraffin. Sections of 5 micron thickness were cut and mounted on slides. Sections were treated by xylene to remove paraffin, hydrated by alternating ethanol and water. Slides were immersed into antigen retrieval buffer (10 mM Sodium citrate, 0.05% Tween 20, pH 6.0) and heated at 100° C. for 15 min. After washed by PBS, the samples were blocked by 5 mg/mL BSA, 5% normal goat serum in PBS for 30 min. Samples were incubated with primary antibody diluted in blocking buffer at 4° C. overnight. Slides were washed by PBS 3×5 min, then incubated with secondary antibody diluted by blocking buffer at room temperature for 30 min. Slides were washed by PBS 6×5 min, then mounted with anti-fade medium and sealed by nail polish. Images were taken by Nikon TE-2000U microscopy or Cytation5 image reader.

Strontium Distribution

Strontium distribution was assayed in several main organs namely the heart, brain, spleen, testes, muscle, lung, kidney, and liver. After euthanization, each organ was collected and stored in −80° C. until analysis. Tissue digestion was carried out by adding 70% nitric acid and 37% hydrogen peroxide to each sample. Samples were uncapped after 1 hour to release built up gas. Tissues were left to digest for 2 days at room temperature. After 2 days, the samples were diluted down to 2.4% acid in MQ water and prepared for ICP-OES as mentioned above.

Elemental Analysis

XPS analysis of the sectioned tissue was conducted on a Thermo Fisher ESCALab 250Xi using Al K-alpha X-ray source (1486.6 eV) (Thermo Fisher Scientific, Waltham Mass.). The monochromated X-ray beam spot size was 300 µm in diameter and the power was 100 watts. A pass energy of 100 eV and step size of 1 eV were used for the survey scan. For the high resolution scan, 50 eV of pass energy and a 0.1 eV step size were used. The dwell time was 50 ms. The XPS spectra were calibrated with adventitious carbon peak at 284.8 eV. All XPS data were processed with Avantage software.

The invention claimed is:

1. A composition comprising a PPCN-based phosphate-displaying hydrogel comprising a polymer of covalently linked citric acid, poly(ethylene glycol), glycerol 1,3-diglycerolate diacrylate, poly-(N-isopropylacrylamide), and β-glycerophosphate monomers.

2. The composition of claim 1, wherein the PPCN-based phosphate-displaying hydrogel comprises the structure:

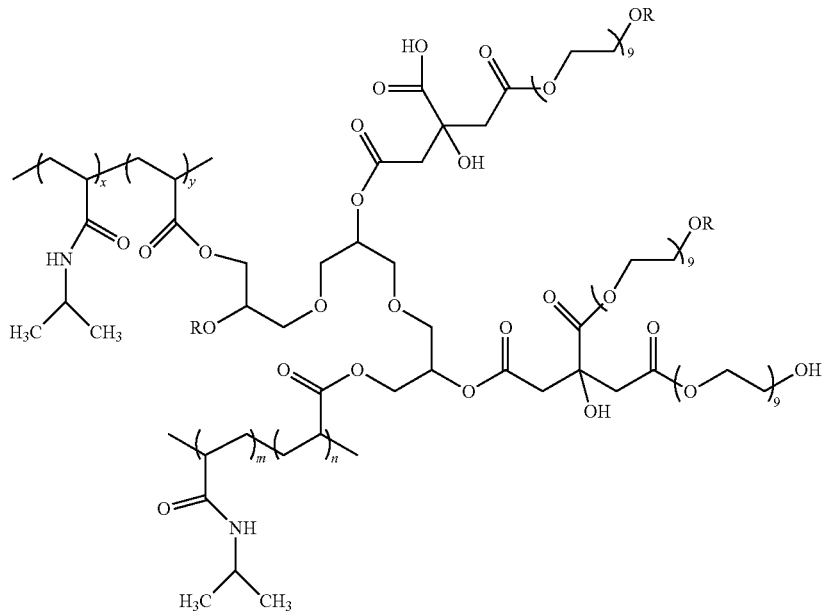

wherein y, m, and n are independently 2-20.

3. The composition of claim 1, prepared by (a) polycondensation of citric acid, poly(ethylene glycol), glycerol 1,3-diglycerolate diacrylate, and β-glycerophosphate monomers; followed by (b) free radical polymerization with poly-(N-isopropylacrylamide).

4. A method of facilitating bone repair comprising administering a composition of claim 1 to fractured or diseased bone site, and allowing the composition to gel.

* * * * *

UNITED STATES PATENT AND TRADEMARK OFFICE
CERTIFICATE OF CORRECTION

PATENT NO. : 11,559,609 B2  
APPLICATION NO. : 16/468224  
DATED : January 24, 2023  
INVENTOR(S) : Guillermo A. Ameer et al.

It is certified that error appears in the above-identified patent and that said Letters Patent is hereby corrected as shown below:

In the Specification

Column 1, Line 15, insert:
--This invention was made with government support under grant number GM105538 awarded by the National Institutes of Health. The government has certain rights in the invention.--

Signed and Sealed this  
Twelfth Day of November, 2024

Katherine Kelly Vidal  
*Director of the United States Patent and Trademark Office*

SEQUENCE LISTING

<160> NUMBER OF SEQ ID NOS: 5

<210> SEQ ID NO 1
<211> LENGTH: 6
<212> TYPE: PRT
<213> ORGANISM: Artificial sequence

```
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = hydroxyproline

<400> SEQUENCE: 1

Gly Phe Xaa Gly Glu Arg
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic peptide

<400> SEQUENCE: 2

Asp Gly Glu Ala
1

<210> SEQ ID NO 3
<211> LENGTH: 7
<212> TYPE: PRT
<213> ORGANISM: Artificial sequence
<220> FEATURE:
<223> OTHER INFORMATION: Synthetic peptide

<400> SEQUENCE: 3

Ser Val Val Tyr Gly Leu Arg
1               5

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

Lys Arg Ser Arg
1

<210> SEQ ID NO 5
<211> LENGTH: 7
<212> TYPE: PRT
<213> ORGANISM: Artificial sequence
<220> FEATURE:
<223> OTHER INFORMATION: Synthetic peptide

<400> SEQUENCE: 5

Phe His Arg Arg Ile Lys Ala
1               5
```